United States Patent
Vashaee et al.

(10) Patent No.: US 10,473,601 B1
(45) Date of Patent: Nov. 12, 2019

(54) SYSTEM AND METHOD FOR SPATIALLY RESOLVED $T_1$-$T_2$ DISTRIBUTION MEASUREMENT

(71) Applicant: University of New Brunswick, Fredericton (CA)

(72) Inventors: Sarah Vashaee, Fredericton (CA); Benedict Newling, Fredericton (CA); Bruce J. Balcom, Fredericton (CA)

(73) Assignee: University of New Brunswick, Fredericton, NB (CA)

(*) Notice: Subject to any disclaimer, the term of this patent is extended or adjusted under 35 U.S.C. 154(b) by 69 days.

(21) Appl. No.: 15/674,887

(22) Filed: Aug. 11, 2017

(51) Int. Cl.
*G01N 24/08* (2006.01)
*G01R 33/50* (2006.01)
*G01R 33/483* (2006.01)

(52) U.S. Cl.
CPC ....... *G01N 24/081* (2013.01); *G01R 33/4833* (2013.01); *G01R 33/50* (2013.01)

(58) Field of Classification Search
CPC ............ G01R 33/4816; G01R 33/4818; G01R 33/482; G01R 33/4822; G01R 33/4824; G01R 33/4826; G01R 33/4828; G01R 33/483; G01R 33/4831; G01R 33/4833; G01R 33/4835; G01R 33/4836; G01R 33/4838; G01R 33/50; G01R 33/543; G01R 33/5602; G01R 33/5604; G01R 33/5605; G01R 33/5607; G01R 33/5608; G01R 33/561; G01R 33/5611; G01R 33/5612; G01R 33/5613; G01R 33/5614; G01R 33/5615; G01R 33/5616; G01R 33/5617

See application file for complete search history.

(56) References Cited

U.S. PATENT DOCUMENTS

| | | | |
|---|---|---|---|
| 6,577,128 B1 * | 6/2003 | Smith .................. | G01R 33/441 324/309 |
| 8,791,695 B2 | 7/2014 | Balcom et al. | |
| 9,069,048 B2 * | 6/2015 | Cull ..................... | G01N 24/088 |

OTHER PUBLICATIONS

A.T. Watson, C.T.P. Chang, Characterizing porous media with NMR methods, Prog. Nucl. Magn. Reson. Spectrosc. 31 (1997) 343-386.
R.L. Kleinberg, W.E. Kenyon, P.P. Mitra, Mechanism of NMR relaxation of fluids in rock, J. Mag. Reson. 108A (2) (1994) 206-214.

(Continued)

*Primary Examiner* — Tung X Nguyen
(74) *Attorney, Agent, or Firm* — Eugene F. Derényi; Fogler, Rubinoff LLP

(57) ABSTRACT

A method and system for generating a magnetic resonance pulse sequence for the investigation of a sample by magnetic resonance, including generating a selective scan comprising an adiabatic inversion magnetic resonance pulse sequence wherein the magnetization is inverted from z to −z inside a frequency band, following the selective scan with a non-selective scan comprising a CPMG magnetic resonance pulse sequence wherein the magnetization is maintained along z, obtaining a first signal from the selective scan, obtaining a second signal from the non-selective scan, and subtracting the first and second signals to obtain a resulting signal with only selected frequency components for slice selective investigation of the sample.

16 Claims, 9 Drawing Sheets

(56) References Cited

OTHER PUBLICATIONS

S. Davies, M.Z. Kalam, K.J. Packer, F.O. Zelaya, Pore-size distributions from nuclear magnetic resonance spin-lattice relaxation measurements of fluid-saturated porous solids. II. Applications to reservoir core samples, J. App. Phys. 67 (1990) 3171-3177.

R.T. Lewis, K. Djurhuus, J.G. Seland, Characterising oil and water in porous media using decay due to diffusion in the internal field, J. Magn. Reson. 259 (2015) 1-9.

M.D. Hurlimann, L. Venkataramanan, C. Flaum, The diffusion-spin relaxation time distribution function as an experimental probe to characterize fluid mixtures in porous media, J. Chem. Phys. 117 (2002) 10223-10232.

Y.Q. Song, L. Venkataramanan, M.D. Hurlimann, M. Flaum, P. Frulla, C. Sraley, T1-T2 correlation spectra obtained using a fast two-dimensional Laplace inversion, J. Mag. Reson. 154 (2002) 261-268.

G. Liao, L. Xiao, R. Xie, Method and experimental study of 2-D NMR logging, Diffusion Fundamentals, 10 (2009) 28.1-28.4.

M. Halse, D.J. Goodyear, B. MacMillan, P. Szomolanyi, D. Matheson, B.J. Balcom, Centric scan Sprite magnetic resonance imaging, J. Magn. Reson. 165 (2003) 219-229.

Y. Zhang, B. Blumich, Spatially resolved D-T2 correlation NMR of porous media, J. Magn. Reson. 242 (2014) 41-48.

M.D. Hurlimann, L. Burcaw, Y.Q. Song, Quantitative characterization of food products by two-dimensional D-T2 and T1-T2 distribution functions in a static gradient, J. Colloid. Interf. Sci. 297 (2006) 303-311.

R.J.S. Brown, R. Chandler, J.A. Jackson, R.L. Kleinberg, M.N. Miller, Z. Paltiel, M.G. Prammer, History of NMR well logging, Concept. Magn. Reson. 13 (2001) 335-413.

M.D. Hurlimann, M. Flaum, L. Venkataramanan, C. Flaum, R. Freedman, G.J. Hirasaki, Diffusion-relaxation distribution functions of sedimentary rocks in different saturation states, Magn. Reson. Imaging, 21 (2003) 305-310.

J. Mitchell, M.D. Hurlimann, E. J. Fordham, A rapid measurement of T1/T2: The DECPMG sequence, J. Mag. Reson. 200 (2009) 198-206.

M.D. Hurlimann, N.J. Heaton, NMR well logging, in: M. Johns, E.O. Fridjonsson, S. Vogt, A. Haber (Eds.), Mobile NMR and MRI: Developments and Applications, Royal Society of Chemistry, Croydon, UK, 2016, pp. 11-85.

J. Mitchell, L.F. Gladden, T.C. Chandrasekera, E.J. Fordham, Low-field permanent magnets for industrial process and quality control, Prog. Nucl. Magn. Reson. Spectrosc. 76 (2014) 1-60.

M.D. Hurlimann, L. Venkataramanan, Quantitative measurement of two dimensional distribution functions of diffusion and relaxation in grossly inhomogeneous fields, J. Magn. Reson. 42 (2002) 31-42.

J. Mitchell, J. Staniland, R. Chassagne, E.J. Fordham, Quantitative in situ enhanced oil recovery monitoring using nuclear magnetic resonance, Transp. Porous. Med. 94 (2012) 683-706.

P.J. McDonald, J.P. Korb, J. Mitchell, L. Monteilhet, Surface relaxation and chemical exchange in hydrating cement pastes: A two-dimensional NMR relaxation study, Phys. Rev. E, 72 (2005) 011409 (1-9).

D. Wweber, J. Mitchell, J. McGregor, L.F. Gladden, Comparing strengths of surface interactions for reactants and solvents in porous catalysts using twodimensional NMR relaxation correlations, J. Phys. Chem. C, 113 (2009) 6610-6615.

M. Fleury, M. Romero-Sarmiento, Characterization of shales using T1-T2 NMR maps, Journal of Petroleum Science and Engineering, J. Petrol Sci. Eng. 137 (2016) 55-62.

K.E. Washburn, J.E. Birdwell, Updated methodology for nuclear magnetic resonance characterization of shales, J. Mag. Reson. 233 (2013) 17-28.

J.P. Korb, G. Ferrante, S. Bubici, M. Mallett, New instrumental platform for the exploitation of the field dependence of T1 in rock core analysis and petroleum fluids : application to T1-T2 correlation maps, diffusion-fundamentals.org, 22 (2014) 1-7.

J.P. Korb, B. Nicot, A. Louis-Joseph, S. Bubici, G. Ferrante, Dynamics and wettability of oil and water in oil shales, J. Phys. Chem. C, 118 (2014), 23212-23218.

A. Tann'us, M. Garwood, Adiabatic pulses, NMR. Biomed. 10 (1997) 423-434.

S. Vashaee, O.V. Petrov, B.J. Balcom, B. Newling, Region of interest selection of long core plug samples by magnetic resonance imaging: profiling and local T2 measurement, Meas. Sci. Technol. 25 (2014) 035004-035014.

S. Vashaee, F. Marica, B. Newling, B. J. Balcom, A comparison of magnetic resonance methods for spatially resolved T2 distribution measurements in porous media, Meas. Sci. Technol. 26 (2015) 055601-055617.

S. Vashaee, B. Newling, B. J. Balcom, Local T2 measurement employing longitudinal Hadamard encoding and adiabatic inversion pulses in porous media, J. Magn. Reson. 261 (2015) 141-148.

F. Goora, B.G. Colpitis, B.J. Balcom, Arbitrary magnetic field gradient waveform correction using an impulse response based pre-equalization technique, J. Magn. Reson. 238 (2014) 70-76.

O.V. Petrov, G. Ersland, B.J. Balcom, Spin echo SPI methods for quantitative analysis of fluids in porous media, J. Mag. Reson. 209 (2011) 39-46.

L. Li, H. Han, B.J. Balcom, Spin Echo SPI methods for quantitative analysis of fluids in porous media, J. Magn. Reson. 198 (2009), 252-260.

\* cited by examiner

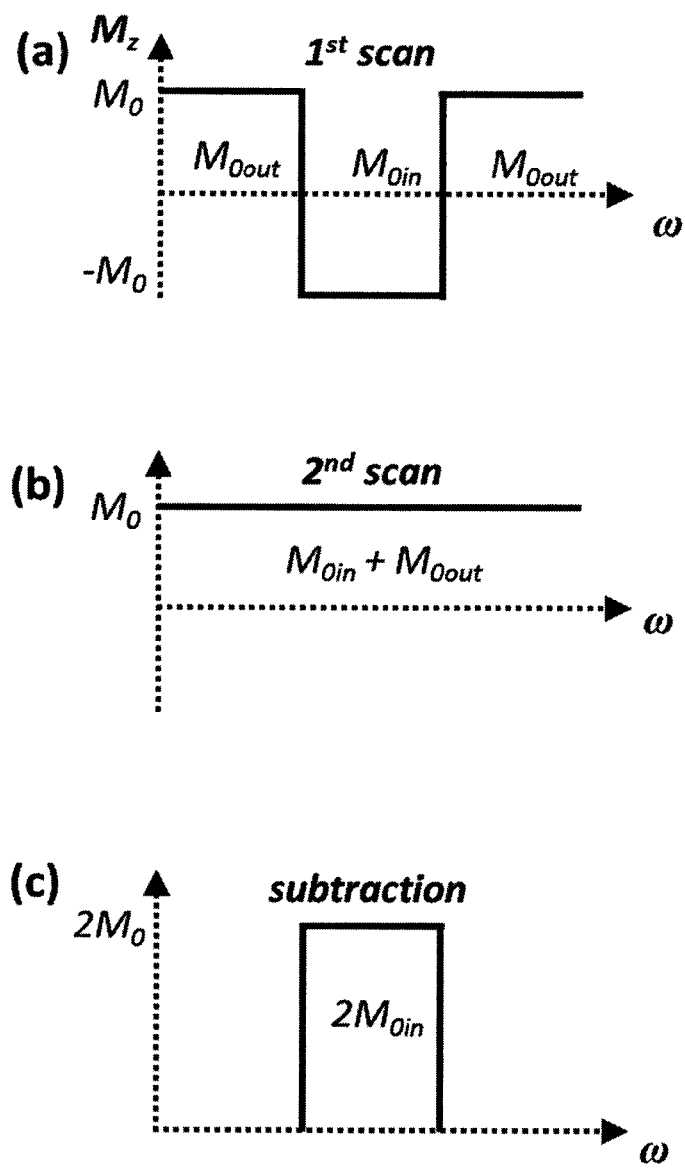
FIG. 2(a)-(c)

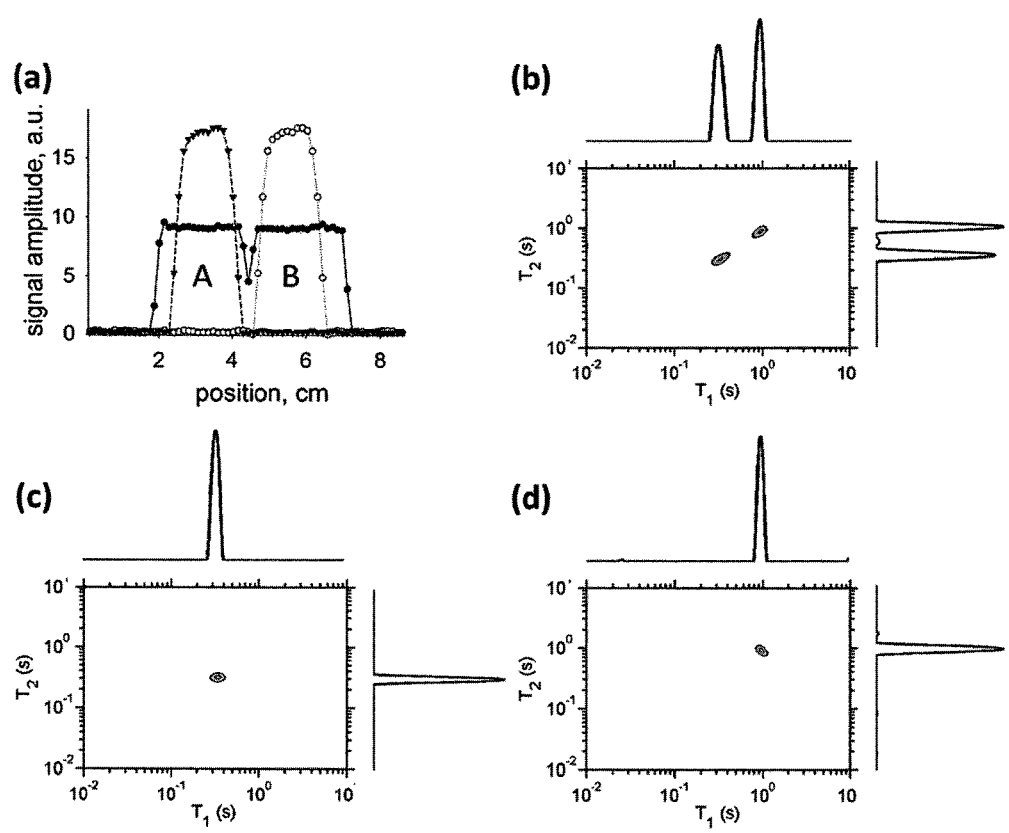
FIGs 3(a)-(d)

SYSTEM AND METHOD FOR SPATIALLY RESOLVED $T_1$-$T_2$ DISTRIBUTION MEASUREMENT

BACKGROUND OF THE INVENTION

Field of the Invention

The present invention relates generally to a system and method for spatially resolved $T_1$-$T_2$ distribution measurement.

Background

Magnetic resonance (MR) is a well-recognised, non-invasive technique for exploring fluid behaviour in reservoir cores and core plugs [1-4]. 2D MR methods [5, 6] are widely employed to identify and quantify hydrocarbon saturation. In comparison with traditional 1D $T_2$ distribution measurement techniques [2-4], 2D MR improves one's ability to separate different fluid phases by mapping proton density as a function of the $T_2$ relaxation time in one dimension and the $T_1$ relaxation time (or diffusion coefficient) in a second dimension.

The D-$T_2$ correlation [5, 7-10] is useful when implemented on low field or portable magnet systems, such as NMR well-logging tools [11, 12]. D-$T_2$ measurement methods permit hydrocarbon and water signal components to be distinguished without chemical shift information [13]. However, in more complex porous media with very small pore sizes, such as shales and many rock samples, D-$T_2$ measurement will fail due to the presence of very short relaxation time components. When the relaxation times are too short, the signal decays before the diffusion information can be encoded [14]. In this case no information on diffusion can be extracted from the signal. The diffusive attenuation by displacement through internal magnetic field gradients complicates the interpretation of diffusion data in porous media [15, 16].

Bulk $T_1$-$T_2$ correlations provide the relaxation time ratio $T_1/T_2$ for reservoir cores and core plugs [6, 13]. $T_1/T_2$ is associated with the strength of surface interaction between the imbibed liquid and a solid pore matrix [17-19]. The ratio $T_1/T_2$ is beneficial as an indicator of wettability [13]. The basic $T_1$-$T_2$ correlation experiment is advantageous for the study of fluids in porous media; the experiment is robust and works well in both low and inhomogeneous magnetic fields [5, 15, 19-23]. The $T_1$-$T_2$ measurement does not require pulsed magnetic field gradients hence the measurement is also free from any effects of gradient induced eddy currents.

Bulk $T_1$-$T_2$ measurements generate information from the whole sample. In some cases spatially resolved $T_1$-$T_2$ measurement of the sample is desired. One example is water flooding experiments in reservoir rock cores and core plugs, where the efficiency of the flooding is examined by monitoring water and oil displacement as a function of space along the core plug.

SUMMARY OF THE DISCLOSURE

In one implementation, the present disclosure is directed to a method for generating a magnetic resonance pulse sequence for the investigation of a sample by magnetic resonance, including generating a selective scan comprising an adiabatic inversion magnetic resonance pulse sequence wherein the magnetization is inverted from z to −z inside a frequency band, following the selective scan with a non-selective scan comprising a CPMG magnetic resonance pulse sequence wherein the magnetization is maintained along z, obtaining a first signal from the selective scan, obtaining a second signal from the non-selective scan, and subtracting the first and second signals to obtain a resulting signal with only selected frequency components for slice selective investigation of the sample. In implementation, the adiabatic inversion magnetic resonance pulse sequence is an adiabatic RF pulse applied in the presence of a magnetic field gradient pulse.

In one implementation, the present disclosure is directed to a slice-selective $T_1$-$T_2$ measurement method for measuring spatially resolved $T_1$-$T_2$ distributions. A spatially selective adiabatic inversion pulse is applied for slice-selection. The slice-selective pulse is able to select a coarse quasi-rectangular slice, on the order of, for example, 5 mm, at a selected position within the sample. A subtraction based on CPMG data acquired with and without adiabatic inversion slice selection is used. $T_1$ weighting is introduced during recovery from the inversion associated with slice selection.

In another implementation, the present disclosure is directed to a spatially-selective adiabatic inversion pulse (a suitable adiabatic inversion pulse is disclosed in reference [24] which is incorporated herein by reference in its entirety) in the presence of a slice-selective magnetic field gradient that is combined with a CPMG measurement to measure $T_1$-$T_2$ for slices of interest. $T_1$ weighting is introduced during recovery from the inversion associated with slice-selection. The inversion pulse is able to select a slice on the order of, for example, 1 cm at a selected position. A subtraction method based on measurements acquired with and without an adiabatic inversion slice-selection.

In other implementations, the present disclosure is directed to characterizing oil-water mixtures and other fluids in porous media, such as, for example, when a coarse spatial distribution of the components is of interest.

In another implementation, the present disclosure is directed to a system for generating a magnetic resonance pulse sequence for the investigation of a sample by magnetic resonance, including an MR imaging system for: generating a selective scan comprising an adiabatic inversion magnetic resonance pulse sequence wherein the magnetization is inverted from z to −z inside a frequency band, following the selective scan with a non-selective scan comprising a CPMG magnetic resonance pulse sequence wherein the magnetization is maintained along z, obtaining a first signal from the selective scan, obtaining a second signal from the non-selective scan, and, an image data processor for subtracting the first and second signals to provide a resulting signal with only selected frequency components for slice selective investigation of the sample. In another implementation, the adiabatic inversion magnetic resonance pulse sequence is an adiabatic RF pulse applied in the presence of a magnetic field gradient pulse.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2(a) depicts a first scan for a slice-selective $T_1$-$T_2$ measurement according to an aspect of the present disclosure;

FIG. 2(b) depicts a second scan for a slice-selective $T_1$-$T_2$ measurement according to an aspect of the present disclosure;

FIG. 2(c) depicts an acquired signal which is the difference between the scans of FIG. 2(a) and FIG. 2(b);

FIG. 3(a) depicts a one-dimensional axial profile of the composite phantom (doped water samples A and B) observed by double half k SPRITE measurement (●). Slice profiles visualized by adiabatic inversion double half k SPRITE are also shown. Doped water samples A (▼) and B (○);

FIG. 3(b) depicts a bulk $T_1$-$T_2$ contour plot for a composite phantom (doped water samples A and B) measured according to method of FIG. 1(a). Projections of f($T_1$, $T_2$) along the $T_1$ and $T_2$ axes are displayed at top and at right;

FIG. 3(c) depicts a slice-selected $T_1$-$T_2$ contour plot for a slice chosen from sample A;

FIG. 3(d) depicts a $T_1$-$T_2$ contour plot for a slice chosen from the sample B;

DETAILED DESCRIPTION

Slice-Selective $T_1$-$T_2$

Figure 1A:
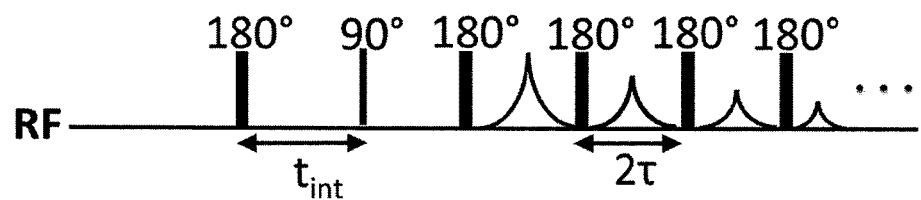
FIG. 1(a) depicts a prior art bulk inversion recovery CPMG approach to measure $T_1$-$T_2$.

In a prior art bulk $T_1$-$T_2$ experiment depicted in FIG. 1(a), the signal is acquired during a CPMG echo train after a $T_1$ inversion recovery [10] and is described by Eq. 1:

$$S(t,t_{int})=\iint dT_1 dT_2 f(T_1,T_2)(1-2\exp\{-t_{int}/T_1\})\exp\{-t/T_2\} \quad [1]$$

where $f(T_1,T_2)$ is the $T_1$-$T_2$ distribution function, t is the cumulative echo time starting at the 90° pulse while $t_{int}$ is the recovery time between the inverting 180° pulse and the subsequent 90° pulse of the CPMG measurement. Data analysis involves a 2D Laplace inversion to extract $f(T_1,T_2)$ from the measured set of echo amplitudes $S(t,t_{int})$.

Figure 1B:
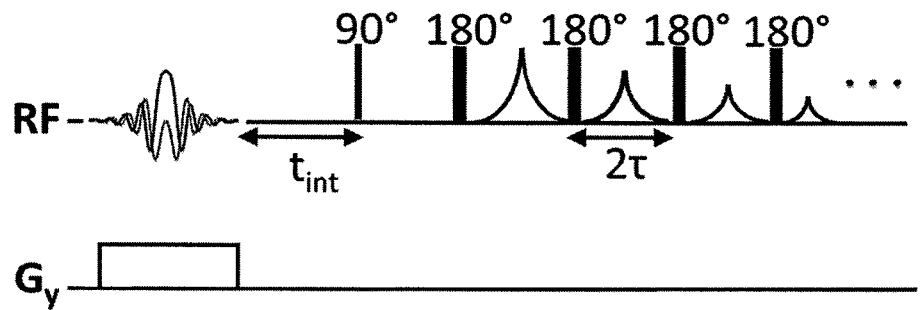
FIG. 1(b) depicts an adiabatic inversion $T_1$-$T_2$ for slice-selective $T_1$-$T_2$ measurements of regions of interest according to an aspect of the present disclosure.

The 180° pulse in a simple $T_1$ inversion recovery measurement is replaced by an adiabatic inversion pulse, depicted in FIG. 1(b), to make the $T_1$-$T_2$ measurement slice-selective. The longitudinal recovery time $t_{int}$ is increased in successive scans. In other embodiments of the present invention, the longitudinal recovery time $t_{int}$ is decreased in successive scans. The adiabatic inversion pulse is applied in the presence of a slice-selective magnetic field gradient. The slice-selective $T_1$-$T_2$ experiment consists of two successive scans: during the 1$^{st}$ (also sometimes referred to in the present disclosure as "first scan" or "selective scan") scan depicted in FIG. 1(b), the magnetization is inverted from z to −z inside a desired frequency band as depicted in FIG. 2(a). During the first scan, the adiabatic inversion pulse rotates the selected frequencies inside the slice of interest by 180°. In FIG. 1(b), $G_y$ indicates a slice selected in the y direction. In other embodiments of the present invention, slices can be selected in another direction (x or y) with a different magnetic field gradient applied. The 2$^{nd}$ (also sometimes referred to in the present disclosure as "second scan" or "non-selective scan") scan, without slice-selection, depicted in FIG. 1(a), is a conventional CPMG pulse sequence with all magnetization maintained along z at the beginning of the measurement depicted in FIG. 2(b). The acquired signal is the difference between the two scans. Subtracting the signals from the 1$^{st}$ and 2$^{nd}$ scans leaves the selected frequency band, as shown in FIG. 2(c).

The transverse magnetization of the nth echo inside the desired frequency band during the $1^{st}$ scan is described by Eq. 2:

$$M_{xy,in} = M_{0,in}(1 - 2\exp\{-t_{int}/T_1\})\exp\{-t/T_2\} \quad [2]$$

where $M_{xy,in}$ and $M_{0,in}$ are transverse and equilibrium longitudinal magnetizations inside the slice of interest. t is the cumulative echo time, and $t_{int}$ is the recovery time between the adiabatic inversion pulse and commencement of the CPMG measurement. The transverse magnetization after the nth echo outside the desired frequency band during the $1^{st}$ scan is described by Eq. 3:

$$M_{xy,out} = M_{0,out}\exp\{-t/T_2\} \quad [3]$$

where $M_{xy,out}$ and $M_{0,out}$ are transverse and equilibrium longitudinal magnetizations outside the slice of interest. The overall transverse magnetization after the $1^{st}$ scan is (inside and outside the slice) described by Eq. 4:

$$M_{xy,1st} = M_{xy,in} + M_{xy,out} = \quad [4]$$
$$M_{0,in}(1 - 2\exp\{-t_{int}/T_1\})\exp\{-t/T_2\} + M_{0,out}\exp(-t/T_2)$$

The transverse magnetization of the nth echo during the $2^{nd}$ scan, method of FIG. 1(a) but without slice-selection (bulk CPMG) is given by Eq. 5:

$$M_{xy,2nd} = M_0 \exp\{-t/T_2\} \quad [5]$$

where $M_{xy}$ and $M_0$, are the transverse and equilibrium longitudinal magnetizations for the whole sample and $M_0 = M_{0,in} + M_{0,out}$. Subtracting Eq. 4 from Eq. 5 gives Eq. 6:

$$M_{xy,2nd} - M_{xy,1st} = 2M_{0,in}\exp\{-t_{int}/T_1\}\exp\{-t/T_2\} \quad [6]$$

which yields the transverse magnetization inside the slice of interest, weighted by $T_1$ and $T_2$. The signal amplitude for the slice of interest is given by Eq. 7:

$$S(t,t_{int}) = \iint dT_1 dT_2 f(T_1,T_2)\exp\{-t_{int}/T_1\}\exp\{-t/T_2\} \quad [7]$$

Where $f(T_1, T_2)$ is the $T_1$-$T_2$ distribution function for the slice of interest.

Experimental Examples

Data Processing

The WinDXP program (Oxford Instruments, Oxford, UK) was employed for $T_2$ distribution determination. WinDXP is a windows-based software toolbox, which allows distributed exponential fitting of data acquired using RINMR (Oxford Instruments, Oxford, UK) data acquisition software.

A two-dimensional Fast Laplace Inversion program (Laplace Inversion Software, Schlumberger-Doll Research) was employed for $T_1$-$T_2$ correlation determination.

Equipment

All MRI measurements were performed on a Maran DRX-HF (Oxford Instruments Ltd, Oxford, UK) 0.2 T permanent magnet which is 8.5 MHz for $^1$H. The RF probe was a custom-built solenoid, 4.4 cm inner diameter, driven by a 1 kW 3445 RF amplifier (TOMCO Technologies, Sydney, Australia). The 90° RF pulses were 11.4 µs with an RF power of 300 W. A shielded three axis gradient coil driven by Techron (Elkhart, Ind.) 7782 gradient amplifiers, provided maximum magnetic field gradients of 25.7 G cm$^{-1}$, 24.7 G cm$^{-1}$ and 33.7 G cm$^{-1}$ in x, y (vertical), and z, respectively.

Bulk $T_1$-$T_2$ and Slice-Selective $T_1$-$T_2$ Measurements of Test Phantoms

Measurements were undertaken on two doped water test phantoms. The phantoms where doped with Gadolinium (III) Chloride hexahydrate (GdCl$_3$.6H$_2$O, Sigma-Aldrich company, USA). The Gadolinium ion concentration was 0.12 mM and 0.04 mM for phantoms A and B, respectively. Physical properties of the test phantoms are reported in Table 1.

TABLE 1

Physical properties of the test phantoms.

| Phantom | $T_1$ (ms) | $T_2$ (ms) | Diameter (cm) | Length (cm) |
|---|---|---|---|---|
| Doped water sample A | 316 | 296 | 3.2 | 2.4 |
| Doped water sample B | 941 | 883 | 3.2 | 2.4 |

The $T_1$ inversion recovery, $T_2$ CPMG and $T_1$-$T_2$ measurements were undertaken with the parameters of Table 2. Measurement time for slice-selective $T_1$-$T_2$ measurement ($1^{st}$ scan plus $2^{nd}$ scan as described herein) was 15.3 minutes.

TABLE 2

Acquisition parameters for MR measurement of the phantoms and brine/crude oil/Bentheimer core plug system.

| Measurement | Doped water sample A | Doped water sample B | Brine/crude oil saturated Bentheimer Core plug |
|---|---|---|---|
| Bulk Inversion recovery | | | |
| $t_{int}$ (ms) | 1-4500 (15 point) | 1-1500 (15 points) | 1-9000 (22 points) |
| Repetition time, TR (s) | 8 | 8 | 17 |
| Averages | 4 | 4 | 8 |
| Measurement time (min) | 8 | 8 | 50 |
| Bulk CPMG | | | |
| Echo time, 2 τ (µs) | 1200 | 1200 | 800 |
| Number of echoes | 3072 | 3072 | 6656 |
| Repetition time, TR (s) | 10 | 10 | 15 |
| Averages | 8 | 8 | 16 |
| Measurement time (min) | 1.3 | 1.3 | 4 |
| Bulk and Slice-selective $T_1$-$T_2$ | | | |
| $t_{int}$ (ms) | 1-4500 (15 point) | 1-4500 (15 point) | 1-9000 (22 points) |
| Echo time, 2 τ (µs) | 1200 | 1200 | 800 |
| Number of echoes | 3072 | 3042 | 6656 |
| Repetition time, TR (s) | 14 | 14 | 24 |
| Averages | 4 | 4 | 8 |
| Measurement time (min) | 14 | 14 | 70 |

An adiabatic inversion pulse (FIG. 1(b)) with duration $T_p = 1.5$ ms and a slice-selective magnetic field gradient pulse of 0.97 G cm$^{-1}$ were employed to select a 1.6 cm slice. The slice-selective magnetic field gradient pulse was pre-equalized [28]. The pre-equalized magnetic field gradient waveform, y direction, with a total duration of 80 ms was defined by 8000 points. The magnetic field gradient as experienced by the sample had a trapezoidal shape and was 1.5 ms in duration. In the current work a 1.6 cm slice was chosen to take advantage of the higher SNR for testing of the new slice-selective $T_1$-$T_2$ method. One can employ a stronger slice-selective magnetic field gradient to reduce the slice thickness with the resolution limited to a slice on the order of 5 mm.

Bulk $T_1$-$T_2$ and Slice-Selective $T_1$-$T_2$ Measurements of Bentheimer Core Plug Fully Saturated with Brine and Crude Oil (Realistic Phantom)

$T_1$ inversion recovery, CPMG, bulk $T_1$-$T_2$ and slice-selective $T_1$-$T_2$ measurements were undertaken on a Bentheimer sandstone core plug (Kocurek Industries, Caldwell, Tex.) fully saturated with 1% NaCl synthetic brine. Bentheimer is a large grain, uniform texture, and high permeability sandstone. The cylindrical Bentheimer rock core-plug sample was 5.2 cm in length and 3.8 cm in diameter. The Bentheimer sandstone core plug was initially saturated under vacuum with brine. Crude oil (Wainwright oil field, Husky Energy, Canada) was injected into the brine-saturated Bentheimer core plug from the top of the sample (vertical y axis perpendicular to the core plug cross section). The final oil saturation was 86%. A Bentheimer sandstone and crude oil were chosen to provide good $T_1$-$T_2$ contrast between water and oil. The $T_1$ inversion recovery, $T_2$ CPMG and $T_1$-$T_2$ measurements were undertaken with the parameters of Table 2. However the measurement time was long (70 minutes) due to long $T_1$ for Bentheimer core plug (1.2 s). 22 $t_{int}$ points were employed for $T_1$ inversion recovery part of $T_1$-$T_2$ measurements (FIG. 1(a) and FIG. 1(b)). One can employ half of this value, 11 points, and still have the same quality $T_1$-$T_2$ plots but with measurement time of 35 minutes.

Slice-Selective $T_1$-$T_2$ Measurements of Bentheimer Core Plug in Different Oil Saturation Stages Crude oil was injected into the brine-saturated Bentheimer sample from the top of the sample. The slice-selective $T_1$-$T_2$ experiment was performed in a measure-inject-measure manner [17] with four different oil saturation stages: 31%, 53%, 68% and 86% crude oil. A known volume of crude oil, corresponding to specified fraction of the core plug pore volume, was injected. The sample was held at static conditions while the MR data were acquired. The next volume of crude oil was injected, and the MR measurement repeated.

$T_1$ inversion recovery, CPMG, bulk $T_1$-$T_2$ and slice-selective $T_1$-$T_2$ measurements were undertaken at each crude oil saturation stage with the parameters of Table 2. The slice-selection parameters were as outlined in section 3.3.

A spin echo single point imaging (SE-SPI) measurement [29, 30] was performed for each crude oil saturation stage to determine the extent of oil penetration. The following parameters were employed: echo time=2000 μs, number of echoes=1024, TR (repetition time)=6 s, field of view=90 mm.

Results and Discussion

Bulk $T_1$-$T_2$ and Slice-Selective $T_1$-$T_2$ Measurements of Test Phantoms

The bulk $T_1$-$T_2$ measurement (FIG. 1(a)) was tested with a composite sample comprising two doped water phantoms. A dhk (double-half-k) SPRITE [31] profile of the composite sample is shown in FIG. 3(a). The bulk $T_1$-$T_2$ plot for the composite sample is shown in FIG. 3b. $T_{1max}$=323 ms and 955 ms, $T_{2max}$=300 ms and 889 ms for doped water samples A and B, respectively. The $T_{1max}$ and $T_{2max}$ values in FIG. 3b are in a good agreement with those measured with conventional $T_1$ inversion recovery and CPMG for the individual phantoms (Table 1).

The broadband 180° pulse in the bulk $T_1$-$T_2$ measurement (FIG. 1(a)) was replaced by an adiabatic inversion pulse (FIG. 1(b)) to measure $T_1$-$T_2$ for two slices, 1.6 cm in width, from the composite phantom. A 1.6 cm slice-width was chosen since the combination of two slices (3.2 cm) encompasses the majority of the sample (excluding the sample edges). Theoretically, one should be able to choose a slice thickness as narrow as possible. One can increase the magnetic field gradient strength to reduce slice thickness while the bandwidth and slice selective pulse duration are fixed. However, increment of slice selective gradient leads to longer stabilization times for magnetic field gradients which will degrades the quality and quantity of the selected slice (slice selective magnetic field gradient is not constant during slice selective pulse application). Minimum slice thickness of 5 mm is suggested.

The adiabatic inversion pulse was employed with a double half-k SPRITE measurement [31] to visualize the slices of interest in the composite phantom (FIG. 3(a)). Individual slices were selected by applying a magnetic field gradient and changing the carrier frequency for the adiabatic inversion pulses.

The $T_1$-$T_2$ plot for a slice corresponding to doped water sample A from the composite sample is shown in FIG. 3(c). Spatially resolved $T_1$-$T_2$ data acquisition and processing parameters were the same as for the bulk $T_1$-$T_2$ measurement. The $T_{1max}$ was 312 ms and the $T_{2max}$ was 303 ms (FIG. 3(c)) which agrees with the reference values reported in Table 1. FIG. 3d illustrates the slice-selective $T_1$-$T_2$ measurement for a slice from the doped water sample B in the composite phantom. The $T_{1max}$ was 948 ms with a $T_{2max}$ of 873 ms (FIG. 3(c)), which once again is in agreement with the reference values reported in Table 1.

The above measurements reveal the accuracy of the slice-selective $T_1$-$T_2$ approach measuring $T_1$-$T_2$ distributions spatially resolved. As expected from Eq. 6, subtraction of the bulk CPMG $T_2$ result (FIG. 1(b) with no slice-selection) and the result of measurement (FIG. 1b) yielded signal only from within the slice of interest. The slice signal is approximately twice that of the original signal as observed for the profile measurements of FIG. 3 (due to subtraction of two scans). The slice length (1.6 cm) is ⅔ of the individual doped water sample length (2.4 cm). Hence the integration of the signal regions coming from the individual slices (FIGS. 3c and 3d) are approximately 4/3 of the bulk $T_1$-$T_2$ signal and show that the method is accurate and quantitative.

Bulk $T_1$-$T_2$ and Slice-Selective $T_1$-$T_2$ Measurements of Bentheimer Core Plug Saturated with Brine and Crude Oil (Uniform Realistic Phantom)

Figure 4:
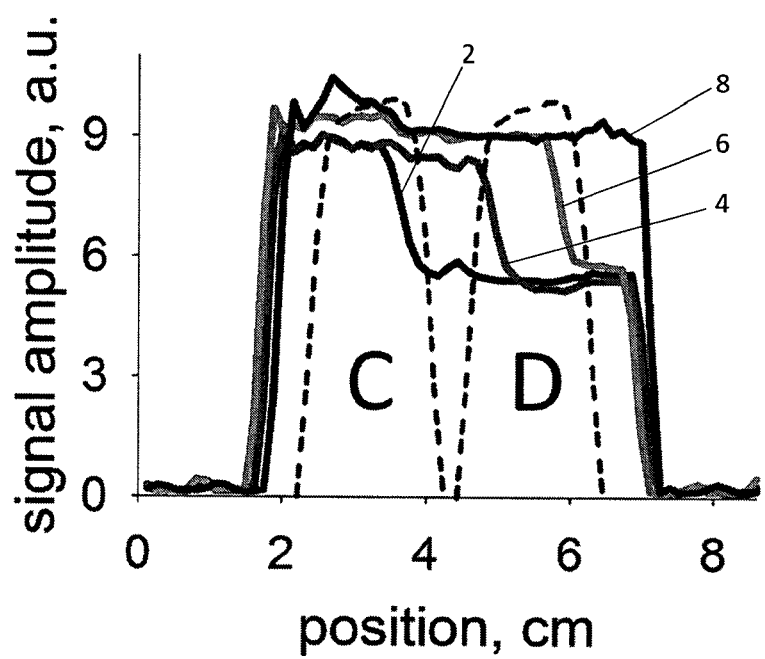
FIG. 4 depicts a one-dimensional axial profiles of a brine saturated Bentheimer core plug injected with oil in four stages. Bentheimer core plug was initially saturated with brine (not shown) and then was injected from the top of the sample (left of the image) with crude oil in four stages: (━, see reference numeral 2) 31% oil saturation, (━, see reference numeral 4) 53% oil saturation, (━, see reference numeral 6) 68% oil saturation and (━, see reference numeral 8) 86% oil saturation. Position of the slices (C and D) are shown (- - -).
Figure 5:
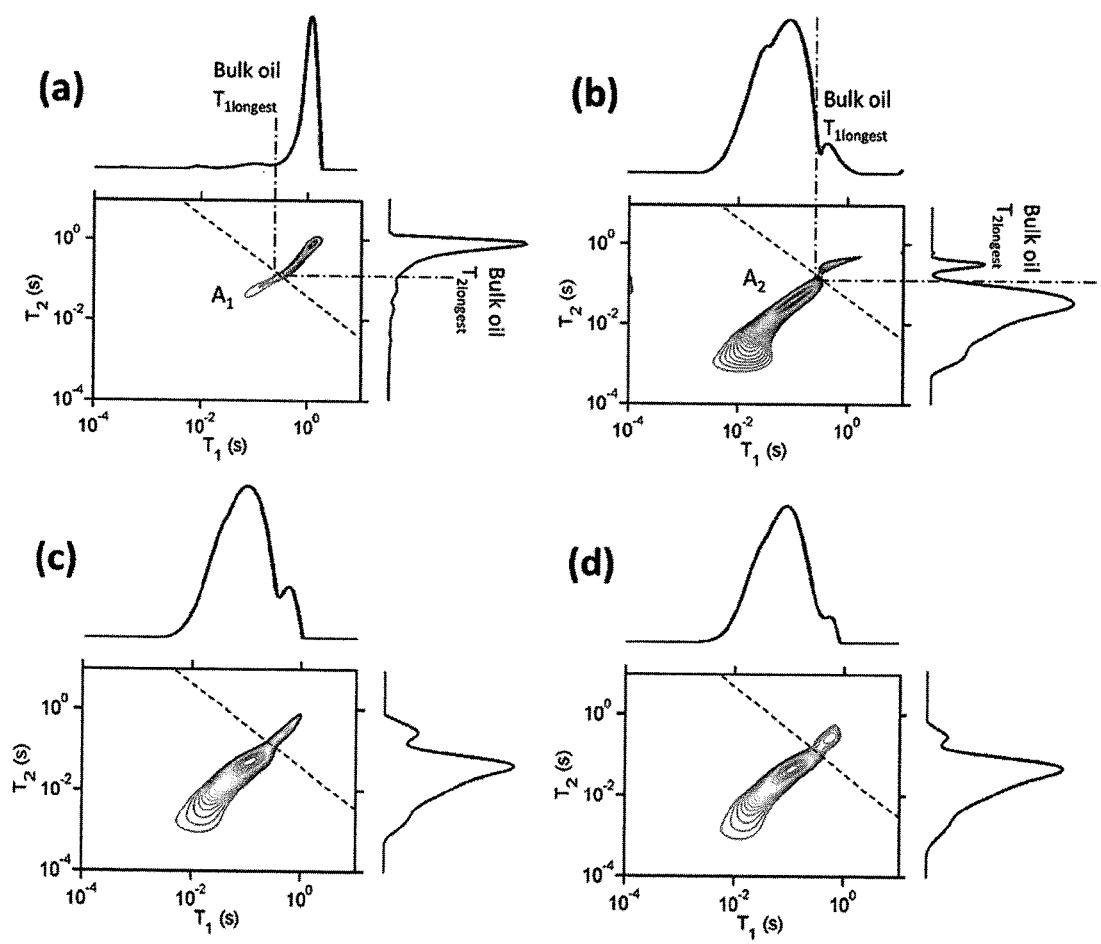
FIG. 5(a) depicts a bulk $T_1$-$T_2$ contour plot for the Bentheimer core plug fully saturated with brine.
FIG. 5(b) depicts a bulk $T_1$-$T_2$ contour plot for the Bentheimer core plug uniformly saturated with brine and oil. (-•-) indicate the bulk crude oil $T_{1longest}$ and $T_{2longest}$. (---) indicate the $T_1$-$T_2$ cut-off which passes through the intersection of (-•-) lines and is parallel to diagonal ($T_1$=$T_2$) line. The $T_1$-$T_2$ plot on left of the (- - -) in FIG. 5(a) denoted by A1 is associated with brine in small pores. The $T_1$-$T_2$ on the left of the (- - -) in FIG. 5(b) denoted by A2 is associated with overlap of oil and brine in small pores. ($A_2$-$A_1$) yields pure oil saturation.
FIG. 5(c) depicts a slice-selective $T_1$-$T_2$ contour plot for a slice chosen from the top of the uniformly saturated with brine and oil Bentheimer core plug (slice C)
FIG. 5(d) depicts a slice-selective $T_1$-$T_2$ contour plot for a slice chosen from the bottom of the sample of FIG. 5(c) (slice D)

To test the ability of the slice-selective $T_1$-$T_2$ approach to measure $T_1$-$T_2$ distributions in porous media, the $T_1$-$T_2$ experiment was undertaken on a brine saturated Bentheimer core plug which was injected with crude oil (100% of the sample includes mixture of oil and brine). Crude oil saturation inside the Bentheimer core plug was measured to be 86% with conventional volumetric measurement. The SE-SPI profile is shown in FIG. 4 (blue line). The 1D profile is fairly uniform which means oil and water are uniformly distributed in the sample. The bulk $T_1$-$T_2$ measurement (FIG. 1a) was utilized to measure bulk oil quantity in the entire core plug and compared to volumetric measurements. The $T_1$-$T_2$ distributions of 100% brine, and partially saturated water and oil in the Bentheimer core plug are shown in FIGS. 5a and 5b.

The $T_1$-$T_2$ plot for partially saturated water and oil in the Bentheimer core plug (FIG. 5b) shows two peaks. The first peak in 2D plots (FIG. 5b) $T_{1max}$=532 ms and $T_{2max}$=350 ms corresponds to brine and the second peak with $T_{1max}$=94 ms and $T_{2max}$=40 ms corresponds to crude oil and residual brine in small pores. MR saturation of oil was determined by integrating the region of the $T_1$-$T_2$ plot corresponding to the oil. As is common, the diagonal dashed line (parallel to $T_1=T_2$ line, not shown) was chosen as the $T_1$-$T_2$ cut-off as explained in the following section.

To determine the $T_1$-$T_2$ cut-off and calculate oil saturation in the sample, it was assumed that relaxation times of S6 oil inside the Bentheimer are the same as bulk S6 oil and that $T_2$ components longer than 100 ms and $T_1$ components longer than 300 ms in the Bentheimer core plug are due to brine not bulk oil. It was also assumed that oil injection will change the interaction between pore surface and fluid (oil and water) in larger pores, but not in smaller pores.

The long dashed dot line (FIGS. 5(a) and 5(b)) show the bulk crude oil $T_{1longest}$ and $T_{2longest}$, 300 ms and 100 ms, respectively. The $T_1$-$T_2$ cut-off passes the intersection of these two lines and is diagonal (parallel to $T_1=T_2$ line).

For the 100% saturated Bentheimer core plug (FIG. 5(a)), the integration of region of $T_1$-$T_2$ distribution which is on left side of the $T_1$-$T_2$ cut-off, A1, with $T_1$<300 and $T_2$<100 ms are assumed to correspond to brine in smaller pores. $A_1$ is 1.3% of the integration of the whole brine signal which is negligible. This region, $A_1$, overlaps with oil $T_1$-$T_2$ distribution in FIG. 5(b). It is assumed that oil injection will not change water in these environments. To calculate pure oil saturation the integration of the regions on the left side of $T_1$-$T_2$ cut-off in FIG. 5(a), $A_1$, will be subtracted from the integration of the region on the left side of the $T_1$-$T_2$ in FIG. 5(b).

The oil saturation after the above correction was 88% which is approximately in agreement with volumetric measurement results (86%).

The $T_1$-$T_2$ measurement (FIG. 1(b)) was applied to generate $T_1$-$T_2$ distributions for two 1.6 slices from the above sample. The slices are illustrated in FIG. 4. $T_1$-$T_2$ plots for a slice from the top of the sample, C, and a slice from bottom of the sample, D, are shown in FIGS. 5c and 5d. The slice-selective $T_1$-$T_2$ plots show two peaks correspond to brine and oil. The $T_{1max}$s and $T_{2max}$S are identical to the ones in FIG. 5(b). The oil saturation for slice C and slice D are 88% and 87%, respectively, which once again is in agreement with the bulk $T_1$-$T_2$ results in FIG. 5(b).

The above results prove the ability of the slice-selective $T_1$-$T_2$ approach to quantitatively measure $T_1$-$T_2$ distributions for different positions in a uniform porous medium sample. The method can discriminate brine and oil which is very useful for understanding recovery processes in petroleum flooding experiments. Two-dimensional MR techniques usually improve the discrimination of the different $^1$H populations because of two contrasts rather than one. The results show that the slice-selective $T_1$-$T_2$ method provides consistent oil saturation results comparable to conventional volumetric methods.

Slice-Selective $T_1$-$T_2$ Measurements of Bentheimer Core Plug at Different Oil Saturation Stages The slice-selective $T_1$-$T_2$ approach (FIG. 1(a)) was implemented to measure oil saturation during a model flooding measurement. The experiment was undertaken on a brine saturated Bentheimer core plug which was injected with crude oil in four stages to displace brine.

The SE-SPI measurement [29, 30] was employed to determine the extent of oil penetration for each oil injection stage (FIG. 4). These profiles were produced from the first echo of each $T_2$ mapping SE-SPI measurement. Recovery delay in SE-SPI was 0.6 s so the separation between the mixture of crude oil/brine and brine signals was observed in the profiles (signal from long $T_1$ water is suppressed). The higher amplitude portion show regions with significant oil saturation. The lower amplitude shows regions still fully saturated with brine which has a longer $T_1$.

The slice-selective $T_1$-$T_2$ measurement (FIG. 1(b)) was implemented to measure oil saturation in slices C and D (FIG. 5) at each stage of oil saturation. One-dimensional profiles for the brine saturated Bentheimer core plug injected with oil in four stages are shown in FIG. 4. $T_1$-$T_2$ distribution plots for slices C and D for different oil saturation stages, are shown in FIGS. 6(a)-6(d) and FIGS. 7(a)-7(d), respectively.

Figure 6:
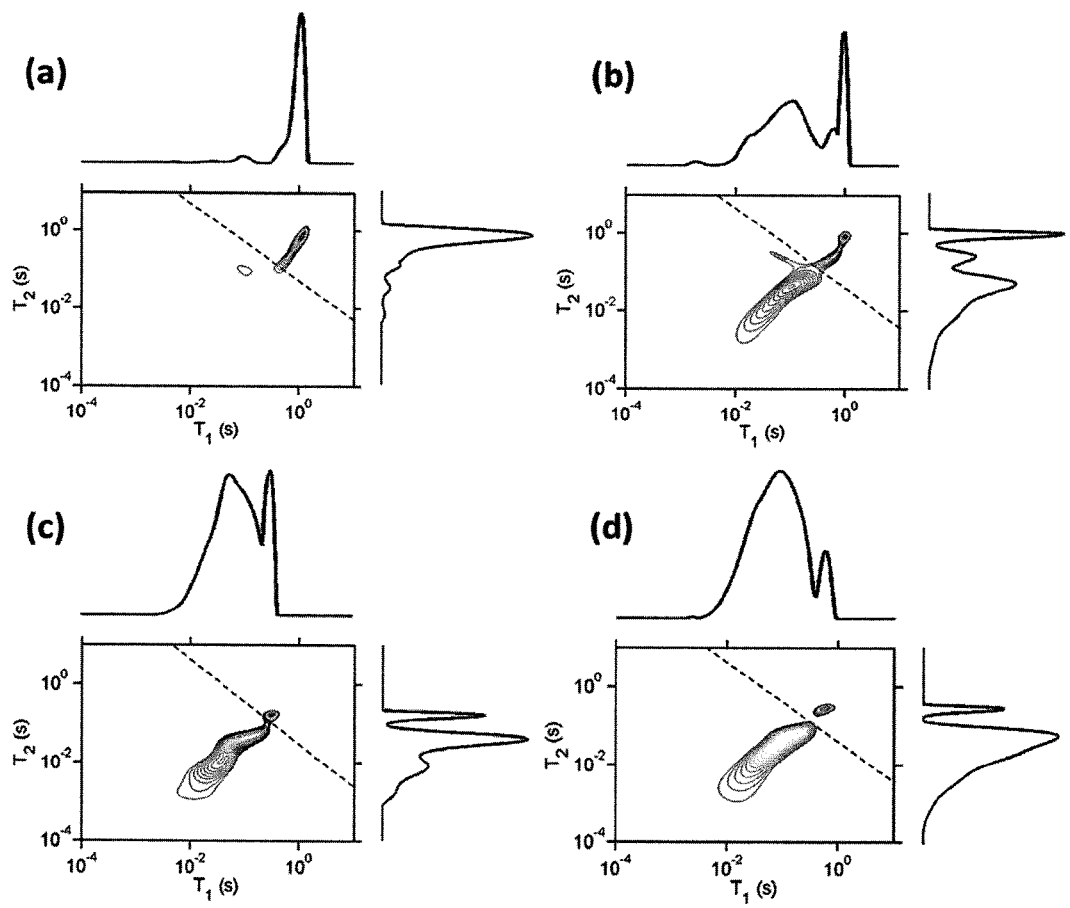
FIG. 6(a) depicts a slice-selective $T_1$-$T_2$ contour plot for slice C for fluids in the Bentheimer core plug with no crude oil (100% brine saturated)
FIG. 6(b) depicts a slice-selective $T_1$-$T_2$ contour plot for slice C for fluids in the Bentheimer core plug with 31% crude oil.
FIG. 6(c) depicts a slice-selective $T_1$-$T_2$ contour plot for slice C for fluids in the Bentheimer core plug with 53% crude oil.
FIG. 6(d) depicts a slice-selective $T_1$-$T_2$ contour plot for slice C for fluids in the Bentheimer core plug with 68% crude oil and (---) indicate the $T_1$-$T_2$ cut-off. $T_1$-$T_2$ plot on left side of (---) is associated with oil and also brine in small pores. $T_1$-$T_2$ plot on right side of (---) corresponds to the brine in partially oil and brine saturated portion of the sample and/or the signal from brine in the fully brine saturated part of the sample.

For the fully brine saturated Bentheimer core plug, as expected, the $T_1$-$T_2$ distributions for both slices (FIGS. 6(a) and 7(a)) are in agreement with that measured with bulk $T_1$-$T_2$ measurement (FIG. 5a).

For the first oil saturation stage (31%) majority of the slice C (FIG. 4, black line) is partially oil and brine saturated and the rest of the slice is fully brine saturated. The $T_1$-$T_2$ plot for the slice C (FIG. 6(b)) shows three peaks. $T_1$-$T_2$ cut-off is shown with dashed line. The $T_1$-$T_2$ plot on the left of the dashed line is mainly attributed to oil and also affected by brine in smaller pores ($T_{1max}$=95 ms and $T_{2max}$=50 ms). The $T_1$-$T_2$ plot on the right of dashed line is associated with brine from the portion of the sample that is partially oil and brine saturated ($T_{1max}$=600 ms and $T_{2max}$=225 ms) and also the signal from brine in the fully brine saturated part of the sample ($T_{1max}$=1.1 s and $T_{2max}$=860 ms). When more oil is injected into the Bentheimer sample during the next oil saturation stages (53%, 68%), 100% of slice C is partially oil and brine saturated (FIGS. 6c and 6d), the $T_{1max}$=1.1 s and $T_{2max}$=860 ms disappears.

Figure 7:
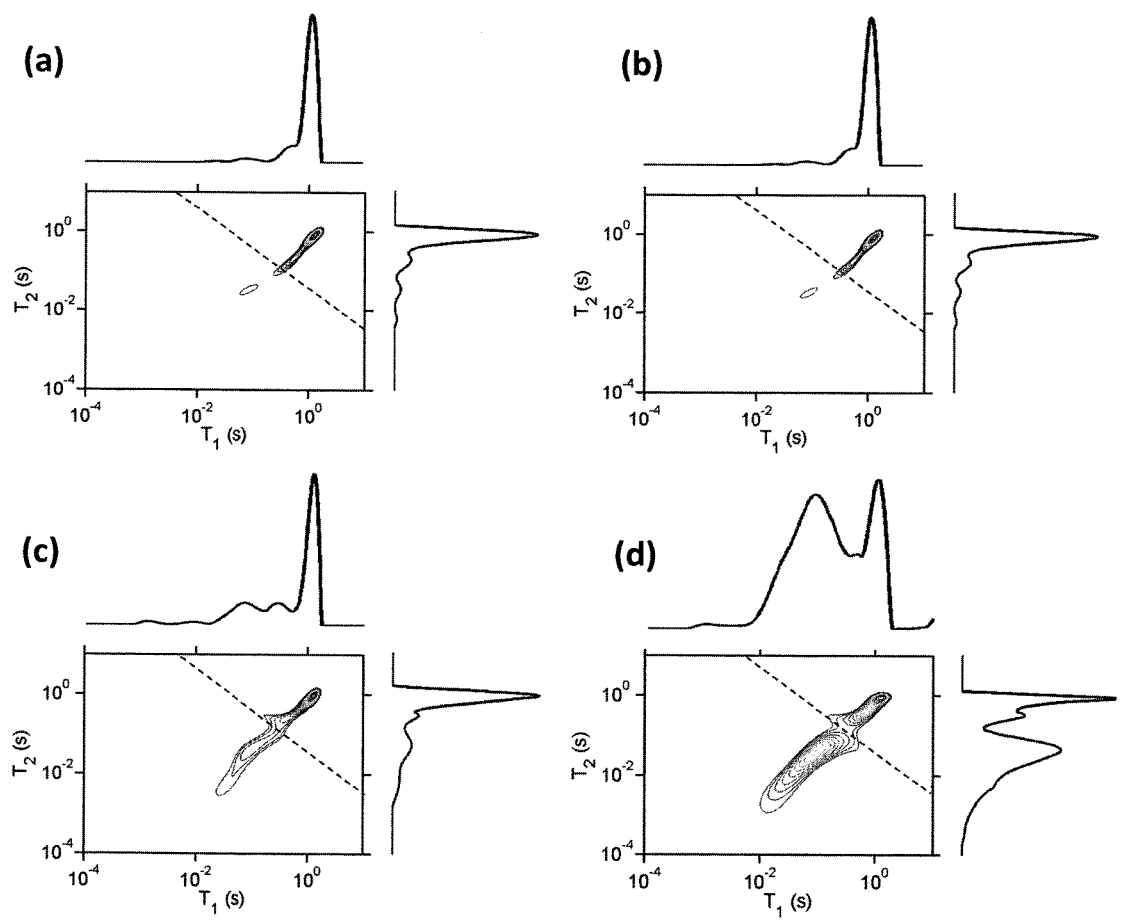
FIG. 7(a) depicts a slice-selective $T_1$-$T_2$ contour plot for a slice chosen from the bottom of the sample (slice D) for fluids in the Bentheimer core plug with no crude oil saturation (100% brine saturated)
FIG. 7(b) depicts a slice-selective $T_1$-$T_2$ contour plot for a slice chosen from the bottom of the sample (slice D) for fluids in the Bentheimer core plug with 31% crude oil saturation.
FIG. 7(c) depicts a slice-selective $T_1$-$T_2$ contour plot for a slice chosen from the bottom of the sample (slice D) for fluids in the Bentheimer core plug with 53% crude oil saturation.
FIG. 7(d) depicts a slice-selective $T_1$-$T_2$ contour plot for a slice chosen from the bottom of the sample (slice D) for fluids in the Bentheimer core plug with 68% crude oil saturation.

The $T_1$-$T_2$ plots for a slice from the bottom of the sample (slice D, FIG. 4) were reproduced for each oil injection stage in FIG. 7. For the fully brine saturated Bentheimer core plug and the first oil saturation stage (31%) the slice selective $T_1$-$T_2$ plots (FIGS. 7(a) and 7(b)) have a peak with $T_{1max}$=1.3 s, 1.4 s and $T_{2max}$=850 ms 920 ms. $T_{1max}$ and $T_{2max}$ values are in agreement with those measured with bulk $T_1$-$T_2$ (FIG. 5a) and the slice-selective $T_1$-$T_2$ measurement result for the slice C (FIG. 6a).

Figure 8:
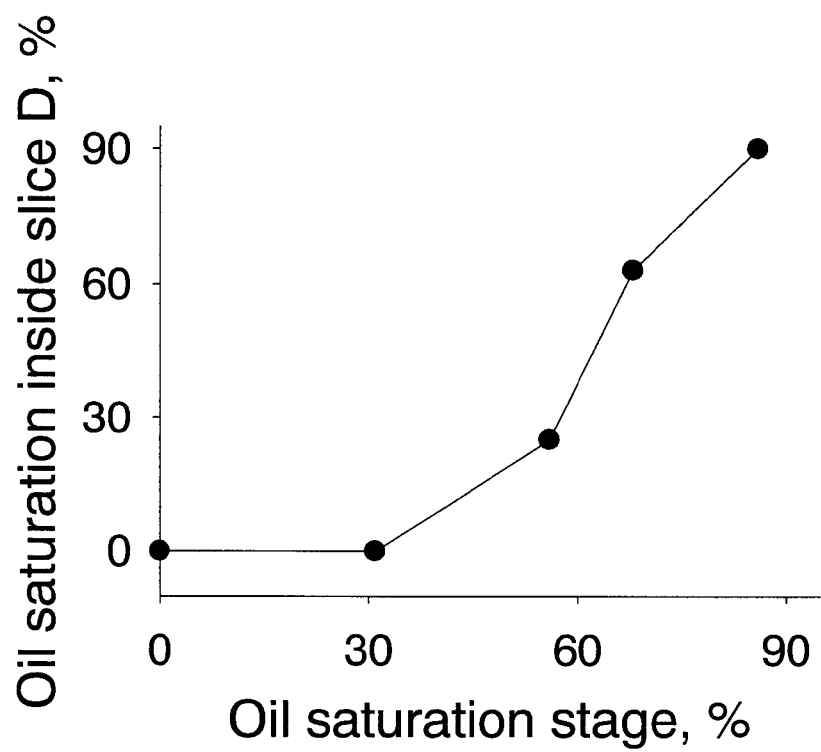
FIG. 8 depicts a graph of oil saturation measured by employing slice-selective $T_1$-$T_2$ versus each oil saturation for slice D, and FIG. 9 schematically shows an MRI measuring system which is suited for carrying out methods according to embodiments of the present invention.

After injecting more oil into the Bentheimer core plug (53%, 68%), oil penetrates into slice as shown in FIG. 4. $T_1$-$T_2$ distribution (FIGS. 8(c) and 8(d)) show three peaks associated with 100% brine saturated portion of the sample, partially oil and brine saturated portion of the sample and oil. Integration of the regions of the slice-selective $T_1$-$T_2$ plots on the left side of the dashed lines after the correction for residual brine signal from small pores yields oil saturation produce oil quantity. FIG. 8 illustrates oil saturation versus oil saturation stage. An increase in oil saturation is observed clearly in slice D.

Figure 9:
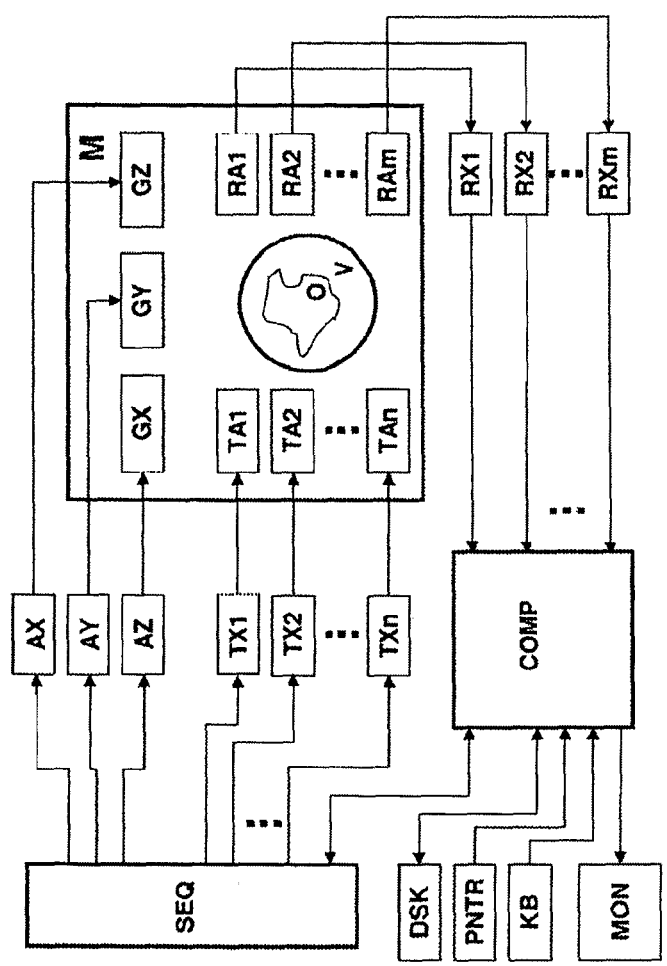

The invention can be implemented in a conventional MRI instrument apparatus as programmed pulse sequences. For example, FIG. 9 schematically shows an MRI measuring system which is suited for performing the inventive method. The system contains a main magnet M for generating the basic magnetic field which is substantially homogeneous and static in a volume under investigation V. Three sets of gradient coils GX, GY, and GZ are introduced into the bore of the main magnet M, which surround the volume under investigation V, and can superpose additional magnetic fields of controllable duration and strength with constant gradients on the basic field. Gradient amplifiers AX, AY, and AZ, which are driven by a sequence control unit SEQ for timely generation of gradient pulses, provide the gradient coils GX, GY, GZ with electric current for generating substantially linear gradient fields.

Several transmitting elements TA1 to TAn are located in the gradient field system, the entirety of which is also called transmitting antenna means. They surround an object under investigation O and are fed by several independent RF power transmitters TX1 ... TXn. The RF pulses generated by these RF power transmitters TX1 ... TXn are determined by the sequence control unit SEQ and triggered at the correct time. The transmitting elements TA1 to TAn irradiate RF pulses onto the object under investigation O located in the volume under investigation V (as described in more detail in FIG. 9), thereby exciting the nuclear spins. The resulting magnetic resonance signals are converted into electric voltage signals using one or more RF receiver elements RA1, ..., RAm, which are then supplied to a corresponding number of receiver units RX1, ..., RXm. The overall receiver elements RA1, ..., RAm are also called receiver antenna means that consists of m receiver elements RA1, ..., RAm. These are also located within the gradient coils GX, GY, GZ and surround the object under investigation O. In order to reduce the expense for equipment, the transmitting and receiver antenna means may also be designed and connected in such a fashion that one or more of the transmitting elements TA1 to TAn are also used for receiving the magnetic resonance signals. In this case, which is not considered in FIG. 9, switching over between transmitting and receiving operation is effected by one or more electronic transmitting-receiver switch points that are controlled by the sequence control unit SEQ. This means that during the RF transmitting phases of the executed RF pulse sequence, this antenna(s) is/are connected to the corresponding RF power transmitter(s) and is/are separated from the allocated receiver channels, while for the receiver phases, the transmitters are separated and the receiver channel is connected. The received signals are amplified by the receiving units RX1 to RXm shown in FIG. 9, and are converted into digital signals using conventional signal processing methods, and passed on to an electronic computer system COMP. In addition to the reconstruction of images and spectra and values derived from the received measured data, the controlling computer system COMP serves to operate the entire MRI measuring system and initiates performance of the pulse sequences through corresponding communication with the sequence control unit SEQ. The user-controlled or automatic execution of programs for adjusting the measuring system properties and/or for generating magnetic resonance images is also provided on this control computer system COMP, as well as the display of the reconstructed images, storage and management of measurement and image data and control programs. In order to perform these tasks, this computer system has at least one processor, one working memory, one computer keyboard KB, one display instrument PNTR, e.g. a computer mouse, one screen MON and one external digital storage unit DSK.

REFERENCES

[1] A. T. Watson, C. T. P. Chang, Characterizing porous media with NMR methods, Prog. Nucl. Magn. Reson. Spectrosc. 31 (1997) 343-386.

[2] R. L. Kleinberg, W. E. Kenyon, P. P. Mitra, Mechanism of NMR relaxation of fluids in rock, J. Mag. Reson. 108A (2) (1994) 206-214.

[3] S. Davies, M. Z. Kalam, K. J. Packer, F. O. Zelaya, Pore II size distributions from nuclear magnetic resonance spin☐lattice relaxation measurements of fluid☐ saturated porous solids. II. Applications to reservoir core samples, J. App. Phys. 67 (1990) 3171-3177.

[4] R. T. Lewis, K. Djurhuus, J. G. Seland, Characterising oil and water in porous media using decay due to diffusion in the internal field, J. Magn. Reson. 259 (2015) 1-9.

[5] M. D. Hurlimann, L. Venkataramanan, C. Flaum, The diffusion-spin relaxation time distribution function as an experimental probe to characterize fluid mixtures in porous media, J. Chem. Phys. 117 (2002) 10223-10232.

[6] Y. Q. Song, L. Venkataramanan, M. D. Hürlimann, M. Flaum, P. Frulla, C. Straley, $T_1$-$T_2$ correlation spectra obtained using a fast two-dimensional Laplace inversion, J. Mag. Reson. 154 (2002) 261-268.

[7] G. Liao, L. Xiao, R. Xie, Method and experimental study of 2-D NMR logging, Diffusion Fundamentals, 10 (2009) 28.1-28.4.

[8] R. G. Coates, L. Xiao, M. G. Prammer, NMR logging principles and applications, Halliburton Energy Services, Houston, US, 1999.

[9] Y. Zhang, B. Blümich, Spatially resolved D-$T_2$ correlation NMR of porous media, J. Magn. Reson. 242 (2014) 41-48.

[10] M. D. Hürlimann, L. Burcaw, Y. Q. Song, Quantitative characterization of food products by two-dimensional D-$T_2$ and $T_1$-$T_2$ distribution functions in a static gradient, J. Colloid. Interf. Sci. 297 (2006) 303-311.

[11] R. J. S. Brown, R. Chandler, J. A. Jackson, R. L. Kleinberg, M. N. Miller, Z. Paltiel, M. G. Prammer, History of NMR well logging, Concept. Magn. Reson. 13 (2001) 335-413.

[12] M. D. Hürlimann, M. Flaum, L. Venkataramanan, C. Flaum, R. Freedman, G. J. Hirasaki, Diffusion-relaxation distribution functions of sedimentary rocks in different saturation states, Magn. Reson. Imaging, 21 (2003) 305-310.

[13] J. Mitchell, M. D. Hürlimann, E. J. Fordham, A rapid measurement of $T_1$/$T_2$: The DECPMG sequence, J. Mag. Reson. 200 (2009) 198-206.

[14] M. D. Hürlimann, N. J. Heaton, NMR well logging, in: M. Johns, E. O. Fridjonsson, S. Vogt, A. Haber (Eds.), Mobile NMR and MRI: Developments and Applications, Royal Society of Chemistry, Croydon, U K, 2016, pp. 11-85.

[15] J. Mitchell, L. F. Gladden, T. C. Chandrasekera, E. J. Fordham, Low-field permanent magnets for industrial process and quality control, Prog. Nucl. Magn. Reson. Spectrosc. 76 (2014) 1-60.

[16] M. D. Hurlimann, L. Venkataramanan, Quantitative measurement of two-dimensional distribution functions of diffusion and relaxation in grossly inhomogeneous fields, J. Magn. Reson. 42 (2002) 31-42.

[17] J. Mitchell, J. Staniland, R. Chassagne, E. J. Fordham, Quantitative in situ enhanced oil recovery monitoring using nuclear magnetic resonance, Transp. Porous. Med. 94 (2012) 683-706.

[18] P. J. McDonald, J. P. Korb, J. Mitchell, L. Monteilhet, Surface relaxation and chemical exchange in hydrating cement pastes: A two-dimensional NMR relaxation study, Phys. Rev. E, 72 (2005) 011409 (1-9).

[19] D. Weber, J. Mitchell, J. McGregor, L. F. Gladden, Comparing strengths of surface interactions for reactants and solvents in porous catalysts using two-dimensional NMR relaxation correlations, J. Phys. Chem. C, 113 (2009) 6610-6615.

[20] M. Fleury, M. Romero-Sarmiento, Characterization of shales using $T_1$-$T_2$ NMR maps, Journal of Petroleum Science and Engineering, J. Petrol Sci. Eng. 137 (2016) 55-62.

[21] K. E. Washburn, J. E. Birdwell, Updated methodology for nuclear magnetic resonance characterization of shales, J. Mag. Reson. 233 (2013) 17-28.

[22] J. P. Korb, G. Ferrante, S. Bubici, M. Mallett, New instrumental platform for the exploitation of the field dependence of $T_1$ in rock core analysis and petroleum fluids: application to $T_1$-$T_2$ correlation maps, diffusion-fundamentals.org, 22 (2014) 1-7.

[23] J. P. Korb, B. Nicot, A. Louis-Joseph, S. Bubici, G. Ferrante, Dynamics and wettability of oil and water in oil shales, J. Phys. Chem. C, 118 (2014), 23212-23218.

[24] A. Tann'us, M. Garwood, Adiabatic pulses, NMR. Biomed. 10 (1997) 423-434.

[25] S. Vashaee, O. V. Petrov, B. J. Balcom, B. Newling, Region of interest selection of long core plug samples by magnetic resonance imaging: profiling and local $T_2$ measurement, Meas. Sci. Technol. 25 (2014) 035004-035014.

[26] S. Vashaee, F. Marica, B. Newling, B. J. Balcom, A comparison of magnetic resonance methods for spatially resolved $T_2$ distribution measurements in porous media, Meas. Sci. Technol. 26 (2015) 055601-055617.

[27] S. Vashaee, B. Newling, B. J. Balcom, Local $T_2$ measurement employing longitudinal Hadamard encoding and adiabatic inversion pulses in porous media, J. Magn. Reson. 261 (2015) 141-148.

[28] F. Goora, B. G. Colpitts, B. J. Balcom, Arbitrary magnetic field gradient waveform correction using an impulse response based pre-equalization technique, J. Magn. Reson. 238 (2014) 70-76.

[29] O. V. Petrov, G. Ersland, B. J. Balcom, Spin echo SPI methods for quantitative analysis of fluids in porous media, J. Mag. Reson. 209 (2011) 39-46.

[30] L. Li, H. Han, B. J. Balcom, Spin Echo SPI methods for quantitative analysis of fluids in porous media, J. Magn. Reson. 198 (2009), 252-260.

[31] M. Halse, D. J. Goodyear, B. MacMillan., P. Szomolanyi, D. Matheson, B. J. Balcom, Centric scan SPRITE magnetic resonance imaging, J. Magn. Reson. 165 (2003) 219-229.

We claim:

1. A method for generating a magnetic resonance pulse sequence for the investigation of a sample by magnetic resonance, comprising:
generating a selective scan comprising an adiabatic inversion magnetic resonance pulse sequence wherein the magnetization is inverted from z to −z inside a frequency band,
following the selective scan with a non-selective scan comprising a CPMG magnetic resonance pulse sequence wherein the magnetization is maintained along z,
obtaining a first signal from the selective scan,
obtaining a second signal from the non-selective scan, and,
subtracting the first and second signals to obtain a resulting signal with only selected frequency components for slice selective investigation of the sample.

2. The method according to claim 1, wherein the adiabatic inversion magnetic resonance pulse sequence is an adiabatic RF pulse applied in the presence of a magnetic field gradient pulse.

3. The method according to claim 2, wherein the overall transverse magnetization after the selective scan is represented by:

$$M_{xy,1st} = M_{xy,in} + M_{xy,out} = \\ M_{0,in}(1 - 2\exp\{-t_{int}/T_1\})\exp\{-t/T_2\} + M_{0,out}\exp(-t/T_2)$$

where $M_{xy,out}$ and $M_{0,out}$ are transverse and equilibrium longitudinal magnetizations outside the slice of interest, wherein the transverse magnetization after the non-selective scan is represented by $$M_{xy,2nd} = M_0 \exp\{-t/T_2\}$$

where $M_{xy}$ and $M_0$, are the transverse and equilibrium longitudinal magnetizations for the whole sample and $M_0 = M_{0,in} M_{0,out}$,
and wherein subtracting the first and second signals yields the transverse magnetization inside the slice of interest, weighted by $T_1$ and $T_2$ represented by $$M_{xy,2nd} - M_{xy,1st} = 2M_{0,in} \exp\{-t_{int}/T_1\}\exp\{-t/T_2\}.$$

4. The method of claim 3, where the signal amplitude for the slice of interest is represented by $$S(t,t_{int}) = \iint dT_1 dT_2 f(T_1,T_2)\exp\{-t_{int}/T_1\})\exp\{-t/T_2\}$$

where $f(T_1,T_2)$ is the $T_1$-$T_2$ distribution function for the slice of interest.

5. The method of claim 4, repeating the selective and non-selecting scans while increasing or decreasing the longitudinal recovery time $t_{int}$.

6. The method of claim 1, wherein the sample is a core from a reservoir.

7. The method of claim 4, further comprising generating spatially resolved $T_1$ and $T_2$ data using 2D inverse Laplace transform.

8. The method of claim 7, further comprising using the $T_1$ and $T_2$ to quantify fluid saturation in a specified region of the sample.

9. A system for generating a magnetic resonance pulse sequence for the investigation of a sample by magnetic resonance, comprising:
an MR imaging system for,
generating a selective scan comprising an adiabatic inversion magnetic resonance pulse sequence wherein the magnetization is inverted from z to −z inside a frequency band,
following the selective scan with a non-selective scan comprising a CPMG magnetic resonance pulse sequence wherein the magnetization is maintained along z,
obtaining a first signal from the selective scan,
obtaining a second signal from the non-selective scan, and,
an image data processor for subtracting the first and second signals to provide a resulting signal with only selected frequency components for slice selective investigation of the sample.

10. The system according to claim 9, wherein the adiabatic inversion magnetic resonance pulse sequence is an adiabatic RF pulse applied in the presence of a magnetic field gradient pulse.

11. The method according to claim 10, wherein the overall transverse magnetization after the selective scan is represented by:

$$M_{xy,1st} = M_{xy,in} + M_{xy,out} = \\ M_{0,in}(1 - 2\exp\{-t_{int}/T_1\})\exp\{-t/T_2\} + M_{0,out}\exp(-t/T_2)$$

where $M_{xy,out}$ and $M_{0,out}$ are transverse and equilibrium longitudinal magnetizations outside the slice of interest, wherein the transverse magnetization after the non-selective scan is represented by $$M_{xy,2nd} = M_0 \exp\{-t/T_2\}$$

where $M_{xy}$ and $M_0$, are the transverse and equilibrium longitudinal magnetizations for the whole sample and $M_0 = M_{0,in} + M_{0,out}$,
and wherein subtracting the first and second signals yields the transverse magnetization inside the slice of interest, weighted by $T_1$ and $T_2$ represented by $$M_{xy,2nd} - M_{xy,1st} = 2M_{0,in} \exp\{-t_{int}/T_1\}\exp\{-t/T_2\}.$$

12. The method of claim 11, where the signal amplitude for the slice of interest is represented by $$S(t,t_{int}) = \iint dT_1 dT_2 f(T_1,T_2)\exp\{-t_{int}/T_1\})\exp\{-t/T_2\}$$

where $f(T_1,T_2)$ is the $T_1$-$T_2$ distribution function for the slice of interest.

13. The method of claim 12, repeating the selective and non-selecting scans while increasing or decreasing the longitudinal recovery time $t_{int}$.

14. The method of claim 9, wherein the sample is a core from a reservoir.

15. The method of claim 12, further comprising generating spatially resolved $T_1$ and $T_2$ data using 2D inverse Laplace transform.

16. The method of claim 15, further comprising using the $T_1$ and $T_2$ to quantify fluid saturation in a specified region of the sample.

* * * * *